United States Patent

Buchel

[11] 3,997,552
[45] Dec. 14, 1976

[54] CHLORINATED IMIDAZOLE DERIVATIVES AND A PROCESS FOR PREPARING THEM

[75] Inventor: Karl Heinz Buchel, Wuppertal, Germany

[73] Assignee: Bayer Aktiengesellschaft, Leverkusen, Germany

[22] Filed: Aug. 7, 1975

[21] Appl. No.: 602,948

[30] Foreign Application Priority Data

Aug. 31, 1974 Germany .......................... 2441820

[52] U.S. Cl. ............................ 260/309; 260/309.6; 260/309.7
[51] Int. Cl.² ........................................ C07D 233/68
[58] Field of Search .................................. 260/309

[56] References Cited
UNITED STATES PATENTS 3,409,606  11/1968  Lutz et al. ........................ 260/309

Primary Examiner—Natalie Trousof
Attorney, Agent, or Firm—Burgess, Dinklage & Sprung

[57] ABSTRACT

Imidazole derivatives, useful as intermediates for making herbicides, having the formula

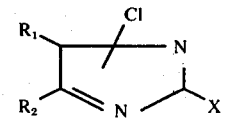

wherein
X is chlorine, lower alkyl mono- or polysubstituted by chlorine, or aryl which is optionally mono- or polysubstituted by halogen and/or lower alkyl and
$R_1$ and $R_2$ are identical or different and are chlorine or phenyl optionally substituted by halogen and/or lower alkyl. The imidazole derivatives are prepared by converting an imidazole derivative having the formula

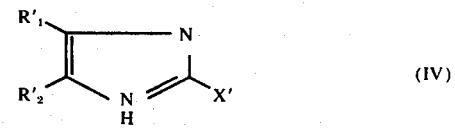

(IV)

wherein
X' is hydrogen, lower alkyl or aryl optionally substituted by halogen atom and/or lower alkyl and
$R'_1$ and $R'_2$ are identical and represent hydrogen and/or phenyl optionally substituted by halogen and/or lower alkyl by means of hydrogen chloride, in the absence of water, into the corresponding hydrochloride, subsequently reacting with hydrochloride with an excess of chlorine at elevated temperature.

10 Claims, No Drawings

CHLORINATED IMIDAZOLE DERIVATIVES AND A PROCESS FOR PREPARING THEM

BACKGROUND

The present invention relates to a new process for the preparation of new chlorinated imidazole derivates and to a process for their preparation. The compounds of the invention can be used as intermediate products for the synthesis of plant protection agents, e.g. herbicides.

It is already known that polybrominated imidazole derivatives, for example 2,4,5-tribromoimidazole, are obtained if imidazole is brominated in ether or chloroform (G. Wyss, Ber. dtsch. chem. Ges. 10, 1365 (1877); J. E. Balaban and F. L. Pyman, J. Chem. Soc. [London] 121, 947 (1922); K. Hofman in: The Chemistry of Heterocyclic Compounds, A. Weissberger Editor, Interscience Publishers, Inc. New York, Vol. 6, page 111 et seq.). The corresponding trichloroimidazole cannot be prepared in this way.

Furthermore it is known that 2,4,5-trichloroimidazole is obtained by heating 2,4,5-tribromoimidazole with concentrated hydrochloric acid (J. Heterocycl. Chem., 399 – 402 (1967)).

It has not hitherto been possible to synthesise other chlorinated imidazole derivatives. Various attempts to arrive at usable results by varying the methods of chlorination, such as, for example, by using chlorine in the presence of $FeCl_3$, by photochlorination, by using chlorine in the presence of sodium hydroxide or amines, or by means of $PCl_5$ or $POCl_3$, have only given brown oils and decomposition products.

SUMMARY

The present invention provides imidazole derivates of the general formula I

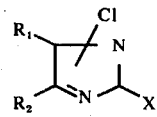     (I)

in which
X represents a chlorine atom, a lower alkyl radical which is monosubstituted or polysubstituted by chlorine, or an aryl radical which is optionally monosubstituted or polysubstituted by halogen and/or lower saturated alkyl radicals and
$R_1$ and $R_2$ are identical or different and represent chlorine or represent a phenyl radical which is optionally substituted by halogen and/or lower alkyl groups.

Advantageously X is straight or branched chain alkyl containing from 1 to 4 carbon atoms optionally mono- or polysubstituted by chlorine or phenyl optionally substituted by at least one of chlorine and methyl.

DESCRIPTION

The general formula I embraces two isomeric structures of the compounds according to the invention, namely that of the corresponding 2-H-imidazole derivatives (formula II) and that of the corresponding 4-H-imidazole derivatives (formula III)

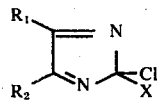   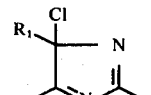

II         III

Where $R_1$ and $R_2$ are identical, the derivatives according to the invention are present in the structure according to the formula II, that is to say as the 2-H-imidazole derivative, a chlorine substituent being located on the imidazole ring in the 2-position.

In the other cases in which $R_1$ and/or $R_2$ represents an optionally substituted phenyl radical, the imidazole derivatives according to the invention are present in the structure of the formula III, that is to say as the 4-H-imidazole derivative, a chlorine substituent being located on the imidazole ring in the 4-position.

The following may be mentioned as examples of compounds which fall within the general formula I: 2,2,4,5-tetrachloro-2H-imidazole, 2-trichloromethyl-2,4,5-trichloro-2H-imidazole, 2-(1,1-dichloroethyl)-, 2-(1,1,2-trichloroethyl)-, 2-(1,1,2,2-tetrachloroethyl)- and 2-(pentachloroethyl)-2,4,5-trichloro-2H-imidazole, 2-phenyl-2,4,5-trichloro-2H-imidazole, 2(4-chlorophenyl)-2,4,5-trichloro-2H-imidazole, 2-(3-bromophenyl)-2,4,5-trichloro-2H-imidazole, 2-(2,4-dichlorophenyl)-2,4,5-trichloro-2H-imidazole, 2-(2-methylphenyl)-2,4,5-trichloro-2H-imidazole, 2-(4-tert.-butyl-phenyl)-2,4,5-trichloro-2H-imidazole, 2-(3,4-diethylphenyl)-2,4,5-trichloro-2H-imidazole, 2-(2,3,4-trimethylphenyl)-2,4-5-trichloro-2H-imidazole, 2-(2-methyl-4-chlorophenyl)-2,4,5-trichloro-2H-imidazole, 2,4-dichloro-4,5-diphenyl-4H-imidazole, 2,4dichloro-4,5-di-(4-chlorophenyl)-4H-imidazole, 2,4-dichloro-4-(2-bromophenyl)-5-(4-bromophenyl)-4H-imidazole, 2,4-dichloro-4-phenyl-5-(3-methylphenyl)-4H-imidazole, 2,4-dichloro-5-phenyl-4-(3-methylphenyl)-4H-imidazole, 2,4-dichloro-4-(2-chlorophenyl)-5-(4-ethylphenyl-4H-imidazole, 2,4-dichloro-5-(2-chlorophenyl)-4-ethylphenyl-4H-imidazole, 4-chloro-2-trichloromethyl-4,5-diphenyl-4H-imidazole, 4-chloro-2-(1,1-dichloroethyl)-4,5(2,4-dibromophenyl)-4H-imidazole, 4-chloro-2,4,5-triphenyl-4H-imidazole, 4-chloro-2,4,5-(4,4,4-trichlorophenyl)-4H-imidazole, 4-chloro-2,4,5-(2,2,2-trimethylphenyl)-4H-imidazole and 4-chloro-2(2-ethylphenyl)-4(3-methylphenyl)-5-phenyl-4H-imidazole.

The compounds according to the invention, of the general formula I, may be obtained if imidazole derivates of the general formula IV

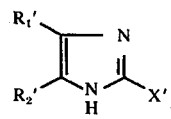   (IV)

in which
X' represents hydrogen, a lower alkyl radical or an aryl radical which is optionally substituted by halogen atoms and/or lower alkyl radicals and $R'_1$ and $R'_2$ are identical and represent hydrogen and/or a phenyl radical which is optionally substituted by halogen and/or lower alkyl groups are converted by means of hydrogen chloride, in the absence of water, into the corresponding hydrochloride, and the latter is subsequently reacted with an excess of chlorine at an elevated temperature.

In the imidazole derivatives used as the starting material, $X'$ preferentially represents hydrogen, a saturated, straight-chain or branched alkyl radical with 1 to 12 carbon atoms an unsubstituted phenyl radical or a phenyl radical which is optionally monosubstituted or polysubstituted by halogen and/or saturated alkyl radicals. Particularly preferentially, $X'$ represents hydrogen, a saturated, straight-chain or branched alkyl radical with 1 to 4 carbon atoms or a phenyl radical. $R_1'$ and/or $R_2'$ preferentially represents hydrogen or an unsubstituted phenyl radical or a phenyl radical which is optionally monosubstituted or disubstituted by halogen and/or straightchain or branched, saturated aliphatic alkyl radicals with 1 to 4 carbon atoms. Particularly preferentially, $R_1'$ and $R_2'$ represent hydrogen or an unsubstituted phenyl radical or a phenyl radical which is optionally substituted by chlorine and/or methyl radicals. Accordingly, the process according to the invention can be used preferentially for the preparation of the corresponding compounds of the formula I, of which the following may be mentioned by way of examples: 2,2,4,5-tetrachloro-2H-imidazole, 2-trichloromethyl-2,4,5-trichloro-2H-imidazole, 2-(1,1-dichloroethyl)-2,4,5-trichloro-2H-imidazole, 2-(1,1-dichloropropyl)-2,4,5-trichloro-2H-imidazole, 2-pentachloroethyl-2,4,5-trichloro-2H-imidazole, 2-phenyl-2,4,5-trichloro-2H-imidazole, 2-(4-chlorophenyl)-2,4,5-trichloro-2H-imidazole, 2-(2,4-dichlorophenyl)-2,4,5-trichloro-2H-imidazole, 2-(2-methylphenyl)-2,4,5-trichloro-2H-imidazole, 2,4-dichloro-4,5-diphenyl-4H-imidazole, 2,4-dichloro-[4-(4-chlorophenyl)-5-phenyl]-4H-imidazole, 2,4-dichloro-[5-(4-chlorophenyl)-4-phenyl]-4H-imidazole, 2,4-dichloro-4,5-di(4-chlorophenyl)-4H-imidazole, 2,4-dichloro-[4-(2-methylphenyl)-5-phenyl]-4H-imidazole, 2,4-dichloro-[5-(2-methylphenyl)-4-phenyl]-4H-imidazole, 4-chloro-2-trichloromethyl-4,5-diphenyl-4H-imidazole, 4-chloro-2-(1,1-dichloroethyl)-4,5-diphenyl-4H-imidazole, 4-chloro-2,4,5-triphenyl-4H-imidazole, 4-chloro-2-(4-methylphenyl)-4,5-diphenyl-4H-imidazole and 4-chloro-2,4,5-(4,4,4-trichlorophenyl)-4H-imidazole.

The following may be mentioned as examples of imidazole derivatives, according to the general formula IV, which are used as starting material: imidazole, 2-methylimidazole, 2-ethylimidazole, 2-isopropylimidazole, 2-sec.-butylimidazole, 2-tert.-butylimidazole, 2-phenylimidazole, 2-(2-chlorophenyl)-imidazole, 2-(2,4-dichlorophenyl)-imidazole, 2-(3-ethylphenyl)-imidazole, 2-(2-chloro-3-methylphenyl)-imidazole, 4,5-diphenylimidazole, 2,4,5-triphenylimidazole, 2-methyl-4,5-diphenylimidazole, 2-ethyl-4,5-diphenylimidazole, 2-tert.butyl-4,5-diphenylimidazole, 4-(2-chlorophenyl)-5-(2'-chlorophenyl)-imidazole, 4-(4-chlorophenyl)-5-(2-methylphenyl)-imidazole, 4-(2-methyl)-5-(2,4-dimethylphenyl)-imidazole, 2-(4-ethylphenyl)-4-(2-chlorophenyl)-imidazole and 5-(2-chlorophenyl)-imidazole.

The imidazole derivatives used as starting material are known (D. Davidson et al, J. Org. Chem. 2, 320–327 (1938); H. Bredereck et al, Chem. Ber. 86, 88–96 (1953); K. Hofmann "The Chemistry of Heterocyclic Compounds," New York, Volume 6, page 33–54, New York (1953) or can be prepared analogously to the reactions described there. Imidazole and 2-methylimidazole are commercially available products.

The course of the reaction can be illustrated, for the example of the reaction of 2-methylimidazole, by the equation which follows, according to which, in accordance with the process of the invention, a hydrochloride is first formed by reaction with hydrogen chloride and is then perchlorinated by reaction with chlorine.

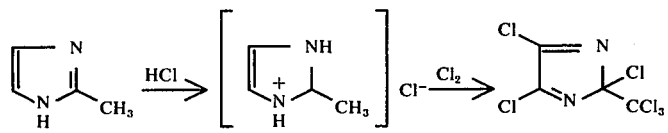

The reaction according to the process of the invention takes place in the absence of water, inert organic solvents generally being used as diluents. Preferred solvents which can be used are ketones such as diethyl ketone, but especially acetone and methyl ethyl ketone; alcohols such as methanol and isopropanol; ethers such as diethyl ether, diisopropyl ether, diisobutyl ether, dibutyl ether, tetrahydrofurane and dioxane; hydrocarbons, such as ligroin, petroleum ether, benzene, toluene and xylene. Particularly preferred solvents are chlorinated aliphatic and aromatic hydrocarbons such as chloroform, carbon tetrachloride, ethylene chloride, methylene chloride and dichlorobenzene.

The reaction of the starting material with hydrogen chloride to give the hydrochloride is generally carried out at room temperature. The subsequent reaction with chlorine takes place at elevated temperature, suitable at the boiling point of the solvent for example from 0° to 250° C, preferably 25° to 150° C. In general, the reaction is carried out under normal pressure but in special cases it can also be advantageous to use superatmospheric pressure or reduced pressure.

In practice, the process according to the invention can be carried out, for example, by first passing hydrogen chloride into the suspension of the imidazole in the solvent until a saturated solution of the particular imidazole hydrochloride has been produced. This is generally achieved at an approximately 10 molar excess of hydrogen chloride. Chlorine is then passed into the solution until the hydrochloride produced has dissolved, which is in general achieved, with 1 mol of imidazole, after passing a normal stream of chlorine for about 80 hours.

Where the imidazole derivative of the general formula IV used as the starting material is substituted in the 2-position by a lower alkyl radical ($X'$), it is possible to obtain, as reaction products, mixtures of compounds of the formula I which are chlorinated to different degrees in the side chain, for example, when using 2-ethylimidazole, 2-(1,1-dichloroethyl)-, 2-(1,1,2-trichloroethyl)-, 2-(1,1,2,2-tetrachloroethyl)- and 2-pentachloroethyl-substituted 2,4,5-trichloro-2H-imidazole. By appropriately controlling the chlorination, for example with respect to temperature, reaction time and possibly concentration, the composition of the resulting mixture can in such cases be influenced in a known manner, so that in each case the desired compound is obtained as the main product.

To isolate the compound according to the invention, the reaction mixture is filtered through sodium sulphate and freed from the solvent by distillation. The oily residue is either fractionally distilled in vacuo or crystallises after trituration.

It must be described as distinctly surprising that according to the reaction of the invention the desired chlorination of the imidazole derivatives takes place with displacement of the position of the double bonds because in the light of the state of the art it had to be expected that in this case again no defined products would be obtained.

The new imidazole derivatives of the formula (I) are accessible in good yields in accordance with the process of the invention and are obtained in good purity, so that purification is in general not necessary if the products are to be reacted further.

The compounds according to the invention are valuable intermediate products for the preparation of plant protection agents and permit simpler methods of synthesis of compounds which are in themselves known and have a herbicidal action. Thus, for example, 2,2,4,5-tetrachloro-2H-imidazole is an intermediate product from which 2,4,5-trichloroimidazole can easily be obtained by catalytic reaction ($H_2/PtO_2$). As is known (Belgian Patent 762,408), 2,4,5-trichloroimidazole exhibits a herbicidal activity. Furthermore, 4-cyano-2,2,5-trichloroimidazole, which also exhibits a herbicidal activity (Belgian Patent 693,680) is obtainable by reaction of 2,2,4,5-tetrachloro-2H-imidazole with anhydrous copper-(I) cyanide.

EXAMPLE 1

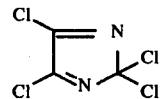

68 g (1 mol) of imidazole were suspended in 3 l of anhydrous carbon tetrachloride. Hydrogen chloride gas was passed in at room temperature for 5 hours, whilst stirring, in the course of which the internal temperature rose slightly (about 30° C). Thereafter the mixture was heated to the boil and chlorine was passed in for 40 hours at the boil. In the course thereof, all the hydrochloride dissolved. The excess chlorine was trapped in a sodium hydroxide solution. After cooling, the solution was filtered through sodium sulphate and carbon tetrachloride was stripped off in a waterpump vacuum. An oily residue remained, which partially crystallised (crude yield 180 g / 84% of theory based on imidazole). The crude product was distilled in a waterpump vacuum, a temperature of at most 120° C being maintained in the distillation flask.

The distillation receiver was cooled by means of an icebath. The distillate thus obtained solidified in the receiver to give colourless crystals.

146 g (68% of theory) of 2,2,4,5-tetrachloro-2H-imidazole (melting point 85° – 87° C / boiling point 70° – 76° C at 12 mm Hg) were obtained.

As a by-product, small amounts of the corresponding dimeric compound

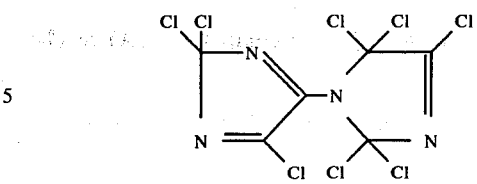

2,2,5-trichloro-4-(2,2,4,5,5-pentachloro-3-imidazolin-1-yl)-2H-imidazole of melting point 149° – 150° C were identified.

Use of 2,2,4,5-tetrachloro-2H-imidazole as an intermediate product for the preparation of 2,4,5-trichloroimidazole:

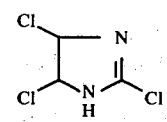

206 g (1 mol) of 2,2,4,5-tetrachloro-2H-imidazole were dissolved in 2 l of anhydrous dioxane and shaken with 4 g of platinum-(IV) oxide for two days under slight hydrogen pressure in a hydrogenation apparatus, until no further hydrogen absorption takes place. The 2,4,5-trichloroimidazole thereby produced had partly precipitated. Methanol was added to the suspension thus obtained until all the trichloroimidazole had dissolved. The solution was then shaken with active charcoal and the active charcoal and catalyst were subsequently filtered off. The filtrate was concentrated by distilling off the solvent in vacuo. The solid residue is dissolved in methanol. Water was added to the solution, whilst stirring, until the trichloroimidazole had precipitated practically completely. The crude product which had precipitated was filtered off and recrystallised from methanol/water.

136 g (79% of theory) of 2,4,5-trichloroimidazole of melting point 191° C were obtained.

Similar results were also obtained on carrying out the reduction with other reducing agents such as, for example, formamide, acetone/hv, benzenesulphinic acid, phenylhydraxzine and HCl/FeCl$_3$.

Use of 2,2,4,5-tetrachloro-2H-imidazole as an intermediate product for the preparation of 4-cyano-2,2,5-trichloroimidazole.

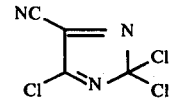

A mixture of 20.5 g (0.1 mol) of 2,2,4,5-tetrachloro-2H-imidazole, 41 g (0.5 mol) of anhydrous copper-(I) cyanide and 230 ml of anhydrous xylene was heated for about 30 hours at 110° – 120° C. After cooling, the reaction mixture was filtered and the brown residue was repeatedly washed with ether. The combined solutions were shaken with active charcoal and the resulting coloured solution was concentrated in vacuo. The concentrated solution was taken up in n-hexane and the product crystallised out. It was filtered off and recrystallised from n-hexane, giving 7.9 g (40% of theory) of 4-cyano-2,2,5-trichloroimidazole (melting point 114° – 115° C).

EXAMPLE 2

A mixture of the following compounds (A) to (D) was prepared.

$$X = \quad \begin{array}{l} -C- \\ Cl_2-CH_3 \end{array} \quad (A)$$

$$-CCl_2-CH_2Cl \quad : \quad (B)$$

$$-CCl_2-CHCl_2 \quad : \quad (C)$$

$$-CCl_2-CCl_3 \quad : \quad (D)$$

48 g (0.5 mol) of 2-ethylimidazole were suspended in 2 l of anhydrous carbon tetrachloride. Hydrogen chloride gas was passed in for 4 hours at room temperature, whilst stirring, in the course of which the internal temperature rose slightly. The mixture was then heated to the boil and chlorine was passed in for 40 hours at the boil. In the course thereof, all the hydrochloride dissolved.

The solvent was stripped off in vacuo (about 10 mm Hg) and the oily residue was purified by distillation in a high vacuum (about $10^{-3} - 10^{-4}$ mm Hg). The distillate thereby obtained was then fractionally distilled in vacuo. In detail, the following fractions were obtained and identified:

1st fraction: 100° – 114° C (12 mm Hg) (first runnings + traces of compound A).

2nd fraction: 114° – 134° C (12 mm Hg) (enriched compound A)

3rd fraction: 134° – 137° C (12 mm Hg) (equal parts of compound A and B)

4th fraction: 137° – 142° C (12 mm Hg) (enriched compound B)

5th fraction: 142° – 152° C (12 mm Hg) (enriched compound C)

EXAMPLE 3

Compound A described in Example 2 was obtained in a pure form from fraction II by again distilling this fraction. The oil, which solidifies in the receiver, is recrystallised from a little pentane, giving colourless crystals; 16 g of 2,4,5-trichloro-2-(1,1-dichloroethyl)-2H-imidazole of boiling point 118° – 125° C/12 mm Hg were obtained.

EXAMPLE 4

Compound B described in Example 2 was obtained in a pure form from fraction IV by again distilling this fraction; 21 g of 2,4,5-trichloro-2-(1,1,2-trichloroethyl)-2H-imidazole of boiling point 141° – 143° C/12 mm Hg were obtained.

EXAMPLE 5

Compound C described in Example 2 was isolated in a purity of about 70% from fraction V by again distilling this fraction; 26 g of 2,4,5-trichloro-2-(1,1,2,2-tetrachloroethyl-2H-imidazole) of boiling point 98°– 103° C/1.5 mm Hg were obtained.

EXAMPLE 6

Fraction III of Example 2 was irradiated with UV light to effect further chlorination. The completely chlorinated compound D was produced, and could be isolated in a pure form by fractional distillation. 32 g of 2,4,5-trichloro-2-pentachloroethyl-2H-imidazole (melting point 74° – 75° C/boiling point 108° – 112° C/1 mm Hg) were thus obtained.

Each of compounds A to D can be made the main product from the start by appropriately controlling the chlorination (concentration, temperature and reaction time).

EXAMPLE 7

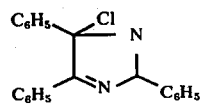

89 g (0.3 mol) of 2,4,5-triphenylimidazole, as starting product, were suspended in 4 l of absolute carbon tetrachloride. Hydrogen chloride gas was passed in at room temperature for 4 hours, whilst stirring, in the course of which the internal temperature rose slightly. The mixture was then heated to the boil and chlorine was passed in for 40 hours at the boil. In the course thereof, all the hydrochloride dissolved. After cooling, the solution was filtered through sodium sulphate and the solvent was stripped off in a waterpump vacuum. The oily yellow residue was dissolved in about 800 ml of absolute ligroin at the boil and the product was crystallised out in the form of yellow crystals by slow cooling. 87 g (88% of theory, based on the starting material) of 4-chloro-2,4,5-triphenyl-4H-imidazole of melting point 129° – 130° C were thus obtained.

EXAMPLE 8 TO 11

The starting materials listed in the table which follows were employed for the reaction in the same way as in Example 7. The end products thereby obtained are defined by the formula, melting point and/or boiling point. Furthermore the yields, relative to starting material, are indicated for the reactions in question.

Table 1

| Example No. | Starting material | End product | Melting point °C | Boiling point °C | Yield |
|---|---|---|---|---|---|
| 8 | | | 66–68 | 113–118/ 12 mm | 79 % |

Table 1-continued

| Example No. | Starting material | End product | Melting point °C | Boiling point °C | Yield |
|---|---|---|---|---|---|
| 9 | | | — | 150–153/ 12 mm | 68 % |
| 10 | | | 81–83 | & — | 65 % |
| 11 | | | 175–177 | — | 63 % |

EXAMPLE 12

Use of the 2,4-dichloro-4,5-diphenyl-4H-imidazole obtainable according to Example 10 as an intermediate product for the preparation of 2,4-diphenylamino-4,5-diphenyl-4H-imidazole.

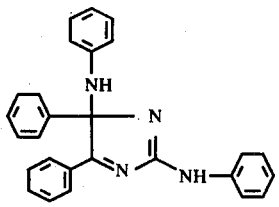

11.2 g (0.12 mol) of aniline are added dropwise, whilst stirring, to 8.7 g (0.03 mol) of 2,4-dichloro-4,5-diphenyl-4H-imidazole in 150 ml of ether. The mixture was then stirred for 20 hours at room temperature. The precipitate produced was filtered off and dried. After adding methylene chloride, the solution was repeatedly washed with water and then dried over sodium sulphate, and the solvent was distilled off. The oily residue crystallised on addition of a little ether. The product obtained was recrystallised from benzene/petroleum ether. 5.2 g (44% of theory) of 2,4-diphenylamino-4,5-diphenyl-4H-imidazole of melting point 153° – 156° C were obtained.

Herbicidal Action of 2,4-diphenylamino-4,5-diphenyl-4H-imidazole:

A post-emergence test and a pre-emergence test were carried out with the solution of active compound described below.

To produce a suitable preparation of active compound, 1 part by weight of the active compound 2,4-diphenylamino-4,5-diphenyl-4H-imidazole is mixed with 5 parts by weight of acetone (out of solvent), 1 part by weight of alkylaryl polyglycol ether was added as emulsifier and the concentrate was then diluted with water to the desired concentration.

Post-emergence Test:

Test plants which have a height of 5 – 15 cm were sprayed with the preparation of the active compound in such a way as to apply the amounts of active compound per unit area which are indicated in Table 2. Depending on the concentration of the spray liquor, the amount of water used is between 1,000 and 2,000 l/ha. After three weeks, the degree of damage listed in Table 2 was determined for the individual plants and characterised by the values 0–5, which have the following meaning:

0 no effect
1 a few slightly burnt spots
2 marked damage to leaves
3 some leaves and parts of stalks partially dead
4 plant partially destroyed
5 plant completely dead

Table 2

| Concentration of the active compound (%) | Degree of damage | | | | |
|---|---|---|---|---|---|
| | Beets | Oats | Mustard | Beans | Cotton |
| 0.2 | 2 | 3 | 3 | 2 | 2 |

Pre-emergence Test

Seeds of the test plants were sown in normal soil and, after 24 hours, watered with the preparation of the active compound. It is expedient to keep constant the amount of water per unit area. The concentration of the active compound in the preparation was of no importance, only the amount of active compound applied per unit area being decisive. After three weeks, the degree of damage to the plants was determined and characterised by the values 0 – 5, which have the following meaning:

0 no effect
1 slight damage or retardation of growth
2 marked damage or inhibition of growth
3 severe damage and only deficient development, or only 50% emerged
4 plants partially destroyed after germination, or only 25% emerged
5 plants completely dead or not emerged.

The amounts used and results can be seen from Table 3 which follows:

Table 3

| Amount of active compound used kg/ha | Degree of damage | | | | |
|---|---|---|---|---|---|
| | Beets | Oats | Cotton | Wheat | Mustard |
| 40 | 2 | 2 | 3 | 2 | 4 |

EXAMPLE 13

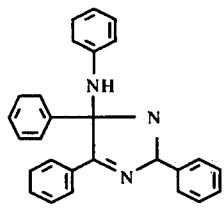

4-phenylamino-2,4,5-triphenyl-4H-imidazole (melting point 157° C) was obtained from 4-chloro-2,4,5-triphenyl-4H-imidazole prepared according to Example 7 and aniline in the same way as in Example 12.

EXAMPLE 14

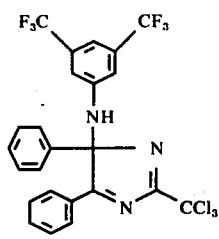

4-(3',5'-di-trifluoromethyl-phenylamino)-4,5-diphenyl-2-trichloromethyl-4H-imidazole (melting point 149°–151° C) was obtained from 4-chloro-4,5-diphenyl-2-trichloromethyl-4H-imidazole prepared according to Example 11 and 3,5-di-trifluoromethyl-aniline in the same way as in Example 12.

EXAMPLE 15

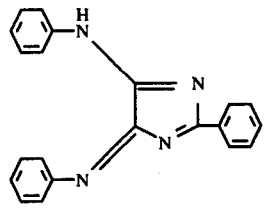

2-phenyl-4-phenylamino-5-phenylimino-5H-imidazole (melting point 201° C) was obtained from 2-phenyl-2,4,5-trichloro-2H-imidazole prepared according to Example 9 and aniline in the same way as in Example 12.

EXAMPLE 16

2.7 g (0.025 mol) 2,4,5-trichloro-2-trichloromethyl-2H-imidazole were dissolved in about 100 ml of absolute carbon tetrachloride. 8 g (0.175 mol) of ethanol were added dropwise under cooling with ice. The solution was then stirred at room temperature during 20 hours. Thereafter the solution was concentrated in vacuo and the crystalline residue was recrystallized from benzene. 3,7 g 4,5-dioxo-2-ethoxy-2-trichloromethyl-imidazolidine of melting point 189°–201° C were obtained.

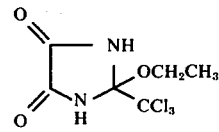

EXAMPLE 17

The products obtained according to Examples 13 – 16 were tested for their herbicidal action in the same way as described in Example 12 for the active compound 2,4-diphenylamino-4,5-diphenyl-4H-imidazole.

The results are listed below in Tables 4 and 5 which follow:

Table 4

| Compound prepared according to Example | concentration of the active compound (%) | (Post-emergence Test) Degree of damage | | | | |
|---|---|---|---|---|---|---|
| | | Beets | Oats | Mustard | Beans | Cotton |
| 13 | 0.2 | 3 | 1 | 2 | 1 | 1 |
| 14 | 0.2 | 4 | 1 | 2 | 1 | 1 |
| 15 | 0.2 | 2 | 1 | 3 | 1 | 1 |
| 16 | 0.2 | 2 | 3 | 4 | 2 | 2 |

Table 5

| Compound prepared according to Example | Amount of active compound used kg/ha | (Pre-emergence Test) Degree of damage | | | | |
|---|---|---|---|---|---|---|
| | | Beets | Oats | Cotton | Wheat | Mustard |
| 13 | 40 | 2 | 1 | 2 | 1 | 3 |
| 14 | 40 | 1 | 2 | 2 | 1 | 2 |
| 15 | 40 | 4 | 4–5 | 4–5 | 4–5 | 4 |
| 16 | 40 | 4–5 | 3 | 4 | 2 | 5 |

The values given for the degree of damage have the same meaning as indicated before.

What is claimed is:

1. Imidazole derivative having the formula

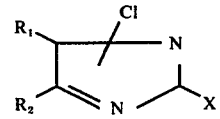

wherein
X is chlorine, lower alkyl mono or polysubstituted by chlorine, or phenyl which is optionally mono or polysubstituted by halogen and/or lower alkyl and $R_1$ and $R_2$ are identical or different and are chlorine or phenyl optionally substituted by at least one of halogen lower alkyl.

2. A 2-H-imidazole derivative according to claim 1.

3. A 4-H-imidazole derivative according to claim 1.

4. Imidazole derivative of claim 1 wherein X is straight or branched chain alkyl containing from 1 to 4 carbon atoms optionally mono- or polysubstituted by chlorine or phenyl optionally substituted by at least one of chlorine methyl.

5. Imidazole derivative of claim 1 selected from the group of 2,2,4,5-tetrachloro-2H-imidazole, 2-trichloromethyl-2,4,5-trichloro-2H-imidazole, 2-(1,1-dichloroethyl)-, 2-(1,1,2-trichloroethyl) -, 2-(1,1,2,2-tetrachloroethyl)- and 2-(pentachloroethyl)-2,4,5-trichloro-2H-imidazole, 2-phenyl-2,4,5-trichloro-2H-imidazole, 2-(4-chlorophenyl)-2,4,5-trichloro-2H-imidazole, 2-(3-bromophenyl)-2,4,5-trichloro-2H-imidazole, 2-(2,4-dichlorophenyl)-2,4,5-trichloro-2H-imidazole, 2-(2-methylphenyl)-2,4,5-trichloro-2H-imidazole, 2-(4-tert.-butyl-phenyl)-2,4,5-trichloro-2H-imidazole, 2-(3,4-diethylphenyl)-2,4,5-trichloro-2H-imidazole, 2-(2,3,4-trimethylphenyl)-2,4,5-trichloro-2H-imidazole, 2-(2-methyl-4-chlorophenyl)-2,4,5-trichloro-2H-imidazole, 2,4-dichloro-4,5-diphenyl-4H-imidazole, 2,4-dichloro-4,5-di-(4-chlorophenyl)-4H-imidazole, 2,4-dichloro-4-(2-bromophenyl)-5-(4-bromophenyl)-4H-imidazole, 2,4-dichloro-4-phenyl-5-(3-methylphenyl)-4H-imidazole, 2,4-dichloro-5-phenyl-4-(3-methylphenyl)-4H-imidazole, 2,4-dichloro-4-(2-chlorophenyl)-5-(4-ethylphenyl-4H-imidazole, 2,4-dichloro-5-(2-chlorophenyl)-4-ethylphenyl-4H-imidazole, 4-chloro-2-trichloromethyl-4,5-diphenyl-4H-imidazole, 4-chloro-2-(1,1-dichloroethyl)-4,5(2,4-dibromophenyl)-4H-imidazole, 4-chloro-2,4,5-triphenyl-4H-imidazole, 4-chloro-2,4,5-(4,4,4-trichlorophenyl)-4H-imidazole, 4-chloro-2,4,5-(2,2,2-trimethylphenyl)-4H-imidazole and 4-chloro-2(2-ethylphenyl)-4(3-methylphenyl)-5-phenyl-4H-imidazole.

6. Process for preparing imidazole derivatives of claim 1 which comprises converting an imidazole derivative having the formula

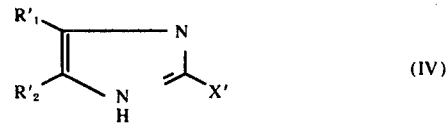

wherein
X' is hydrogen, lower alkyl or phenyl optionally substituted by at least one of a halogen atom lower alkyl and
$R'_1$ and $R'_2$ are identical and represent hydrogen or phenyl optionally substituted by at least one of halogen and lower alkyl by means of hydrogen chloride, in the absence of water, into the corresponding hydrochloride, subsequently reacting said hydrochloride with an excess of chlorine at elevated temperature.

7. Process of claim 6 wherein X' is hydrogen, saturated straight-chain or branched alkyl with 1 to 12 carbon atoms, unsubstituted phenyl or phenyl optionally mono- or polysubstituted by at least one of halogen and alkyl and $R'_1$ and/or $R'_2$ individually are hydrogen or phenyl which is unsubstituted or optionally mono- or disubstituted by at least one of halogen and straight-chain or branched saturated aliphatic alkyl with 1 to 4 carbon atoms.

8. Process of claim 6 wherein the compound of the formula IV is imidazole, 2-methylimidazole, 2-ethylimidazole, 2-iso-propylimidazole, 2-sec.-butylimidazole, 2-tert.-butylimidazole, 2-phenylimidazole, 2-(2-chlorophenyl)- imidazole, 2-(2,4-dichlorophenyl)-imidazole, 2-(3-ethylphenyl)-imidazole, 2-(2-chloro-3-methylphenyl)-imidazole, 4,5-diphenylimidazole,
2,4,5-triphenylimidazole, 2-methyl-4,5-diphenylimidazole, 2-ethyl-4,5-diphenylimidazole, 2-tert.-butyl-4,5-diphenylimidazole,
4-(2-chlorophenyl)-5-(2'-chlorophenyl)-imidazole, 4-(4-chlorophenyl)-5-(2-methylphenyl)-imidazole, 4-(2-methyl)-5-(2,4-dimethylphenyl)-imidazole, 2-(4-ethylphenyl)-4-(2-chlorophenyl)-imidazole or 5-(2-chlorophenyl)-imidazole.

9. Process of claim 6 wherein the reaction is effected in an inert organic solvent.

10. Process of claim 9 wherein the treatment with hydrogen chloride is carried out at ambient temperatures and the reaction with chlorine is effected at the boiling point of the solvent.

* * * * *

UNITED STATES PATENT AND TRADEMARK OFFICE
CERTIFICATE OF CORRECTION

PATENT NO. : 3,997,552
DATED : December 14, 1976
INVENTOR(S) : Karl Heinz Buchel     (Page 1 of 2)

It is certified that error appears in the above-identified patent and that said Letters Patent are hereby corrected as shown below:

Abstract, second to last line    Change "with"(first occurrence) to -- said --.

Col. 1, line 40    Change 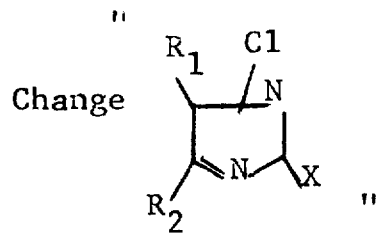

to-- 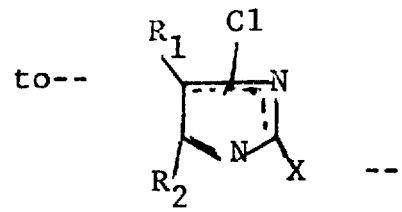

Col. 7, lines 10 & 11    Change "X = —C—Cl$_2$—CH$_3$" to --X = -CCl$_2$-CH$_3$--

Col. 12, claim 1    Change 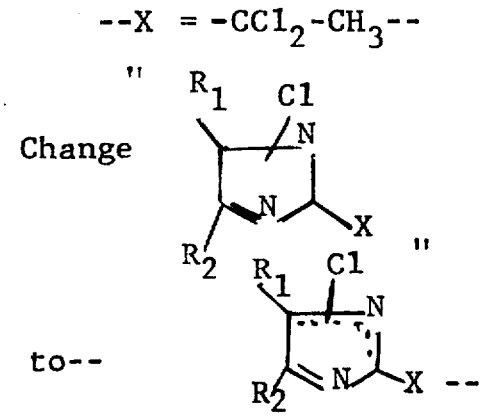

to-- --

UNITED STATES PATENT AND TRADEMARK OFFICE
CERTIFICATE OF CORRECTION

PATENT NO. : 3,997,552
DATED : December 14, 1976
INVENTOR(S) : Karl Heinz Buchel                    (Page 2 of 2)

It is certified that error appears in the above-identified patent and that said Letters Patent are hereby corrected as shown below:

Col. 12, line 67        After "halogen" insert --and--

Col. 13, line 7         After "chlorine" insert --and--

Col. 14, line 9         After "atom" insert --and--

Signed and Sealed this

Seventh Day of February 1978

[SEAL]

Attest:

RUTH C. MASON
Attesting Officer

LUTRELLE F. PARKER
Acting Commissioner of Patents and Trademarks